(12) United States Patent
Rodier et al.

(10) Patent No.: US 7,648,573 B2
(45) Date of Patent: Jan. 19, 2010

(54) WETTING AGENT BASED ON A MIXTURE OF MONOESTERS AND DIESTERS OF BUTYLENE GLYCOL

(75) Inventors: Jean-David Rodier, Villeurbanne (FR); Vincent Hubiche, Saint Laurent de Mure (FR)

(73) Assignee: Gattefosse SAS, St. Priest (FR)

( * ) Notice: Subject to any disclaimer, the term of this patent is extended or adjusted under 35 U.S.C. 154(b) by 346 days.

(21) Appl. No.: 11/718,276

(22) PCT Filed: Sep. 29, 2005

(86) PCT No.: PCT/FR2005/050796

§ 371 (c)(1),
(2), (4) Date: Apr. 30, 2007

(87) PCT Pub. No.: WO2006/048563

PCT Pub. Date: May 11, 2006

(65) Prior Publication Data

US 2009/0023818 A1    Jan. 22, 2009

(30) Foreign Application Priority Data

Nov. 5, 2004  (FR) ................... 04 52547
Mar. 8, 2005  (FR) ................... 05 50604

(51) Int. Cl.
*C09B 67/00* (2006.01)
*C09B 67/20* (2006.01)
*C08K 5/10* (2006.01)
*A61K 8/37* (2006.01)
*A61K 8/04* (2006.01)

(52) U.S. Cl. ........................... 106/504; 106/499
(58) Field of Classification Search ................ 106/499, 106/504

See application file for complete search history.

(56) References Cited

U.S. PATENT DOCUMENTS

| 5,006,617 | A | * | 4/1991 | Engel et al. ................... 526/87 |
| 5,928,652 | A |   | 7/1999 | Bodelin-LeComte |
| 6,649,688 | B1 | * | 11/2003 | Mayer et al. ................. 524/558 |
| 6,653,394 | B1 | * | 11/2003 | Meisenburg et al. ........ 524/589 |
| 6,720,384 | B1 | * | 4/2004 | Mayer et al. ................. 524/591 |
| 6,946,515 | B1 | * | 9/2005 | Lettmann et al. ............ 524/591 |
| 2006/0051486 | A1 | * | 3/2006 | Dowdell et al. .............. 426/601 |
| 2008/0019932 | A1 | * | 1/2008 | Crosby et al. ................. 424/63 |

FOREIGN PATENT DOCUMENTS

| DE | 199 56 603 | 5/2001 |
| EP | 792633 | 9/1997 |
| EP | 0651 990 | 10/1998 |
| EP | 0 860 164 | 12/2001 |
| EP | 1230910 | 8/2002 |
| JP | 57072907 | 5/1982 |

OTHER PUBLICATIONS

Gattefosse Cocoate BG MSDS, printing dated of Apr. 27, 2005.*
Anonymous: "AddiActive—Gattefosse: Formulation(s), Soin Reveil JB 1686/A" Internet Article.

* cited by examiner

*Primary Examiner*—Anthony J Green
(74) *Attorney, Agent, or Firm*—Heslin Rothenberg Farley & Mesiti P.C.

(57) ABSTRACT

Pigment wetting agent contains a mixture of monoesters and diesters of butylene glycol and fatty acids.

14 Claims, 3 Drawing Sheets

WETTING AGENT BASED ON A MIXTURE OF MONOESTERS AND DIESTERS OF BUTYLENE GLYCOL

CROSS-REFERENCE TO RELATED APPLICATIONS

This application is a Section 371 filing of International Application PCT/FR2005/050796 filed on Sep. 29, 2005 and published, in French, as International Publication No. WO 2006/048563 on May 11, 2006, which claims priority from French application no. 0452547 filed on Nov. 5, 2004, which applications are hereby incorporated by reference herein, in their entirety.

BACKGROUND ART

The invention relates to a novel wetting agent for use particularly but in a non-limiting manner, in the field of cosmetics, for its aptitude to wet pigments. This property is particularly sought after in compositions requiring a dispersion of pigments. This is the case in particular of solar products and make-up products. It is also useful in make-up cleansing products to promote the fixation and removal of the pigments present on the skin.

Numerous products are proposed for their aptitude to wet pigments. $C_{12}$-$C_{15}$ alkyl benzoate and isopropyl palmitate are known in particular. Also used for this function are certain triglycerides, such as castor oil and glycerol tricaprylocaprate.

Document EP-A-792 633 describes a powdery anhydrous composition comprising a binder or wetting agent. In practice, the binder is an ester, liquid at ambient temperature, comprising at least two hydrocarbon chains, each comprising at least ten carbon atoms. The ester in question does not have a hydroxyl group. A preferred agent is, for example, glycerol triisostearate.

All the wetting agents known to the Applicant, as previously listed, have a number of drawbacks. Firstly, the quantity of raw material required to wet a given pigment remains relatively high. It affects the formulation in terms of cost, composition and sensory properties. The high viscosity of certain raw materials, such as castor oil, at ambient temperature, or of the pigment dispersions obtained, make these products difficult to handle. Finally, the known wetting agents confer a sometimes greasy touch on the final composition into which they are introduced.

In other words, a need exists, particularly for the cosmetics market, for products having a wetting power that does not have the above drawbacks.

In the course of its researches, the Applicant found that mixtures of monoesters and diesters of butylene glycol, including for example butylene glycol cocoate, had a higher wetting power than that of the known agents.

Butylene glycol cocoate (BGC) is a known product, already used as a cosmetic ingredient in a composition, marketed by the Applicant under the trade name EMULFREE® CBG. More precisely, this composition corresponds to the combination of BGC with isostearyl alcohol and ethylcellulose. In practice, EMULFREE® CBG is used as a stabilizer of the oily phase in the oil-in-water emulsions. The role of the butylene glycol cocoate in this composition is confined to the solubilization of the gelling polymer, that is ethylcellulose. In other words and contrary to the invention, butylene glycol cocoate is not suitable for direct mixing with fillers but is necessarily used in combination with a fatty alcohol (isostearyl alcohol) in the presence of a polymer (ethylcellulose).

The mixture of the invention is clearly distinguished not only in terms of function, but also in terms of structure, from the butylene glycol esters described in document EP-A-860 164. In fact, the document describes the combination of a chemical UV filter with butylene glycol diesters only, with fatty acids containing 6 to 12 carbon atoms. Not only does the composition not contain monoesters, but furthermore, it is used as a chemical filter solubilizing agent and not as a wetting agent.

Document JP 57072907 describes a make-up cleansing product based either on monoesters or on diesters containing 17 to 36 carbon atoms. Here also, the mixture of monoesters and diesters is not also considered. Moreover, in the case of the diesters, they are diacid esters, that is, of an acid esterified by two alcohols and not a diol esterified by two acids, as is the case of the invention. As to the monoesters, they issue from a monoacid with a monoalcohol and not from a monoester of a diol.

Document EP-A-651 990 describes the use of esters in a make-up cleansing composition. According to this document, the esters used are also either monoalcohol esters, or diesters. In practice, they are obtained from an alcohol containing 1 to 17 carbon atoms and a fatty acid containing 3 to 18 carbon atoms. Moreover, they must have a free hydroxyl group.

Document EP-A-1 230 910 describes an oil-in-water emulsion containing pigments, whereof the oily phase only contains caprylocaprate diesters of butylene glycol.

In other words, nothing in the prior art known to the Applicant discloses the idea of using a mixture of monoesters and diesters of butylene glycol, as a wetting agent.

DETAILED DESCRIPTION OF THE INVENTION

Brief Summary of the Invention

Figure 1A:
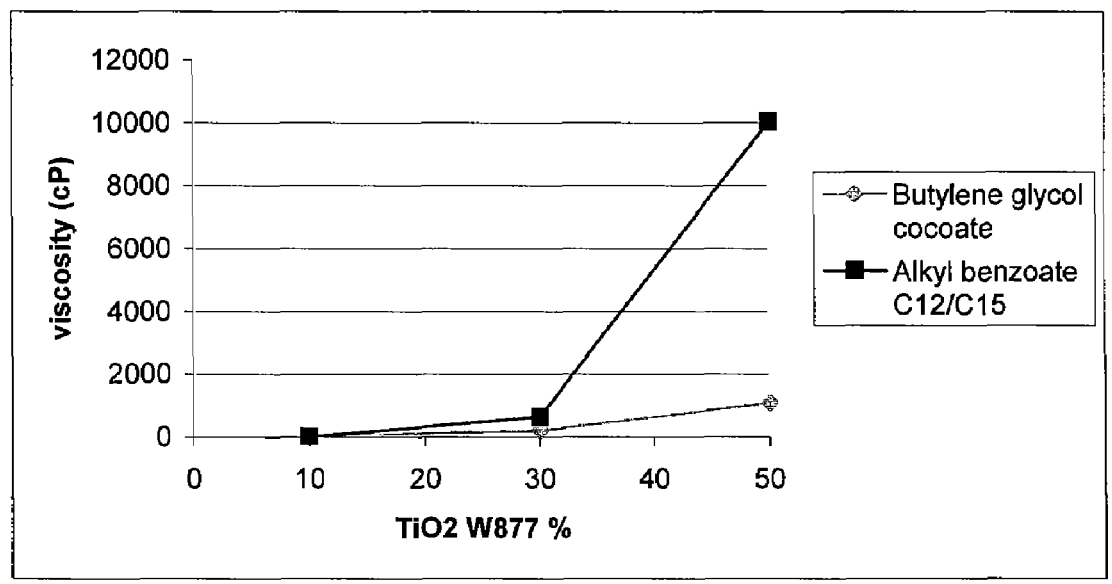
FIGS. 1a, b, c and d are curves showing the viscosity of a dispersion formulated with the wetting agent of the invention or an agent of the prior art ($C_{12}$ to $C_{15}$ alkyl benzoate or castor oil) as a function of an increasing quantity of pigments.
Figure 1B:
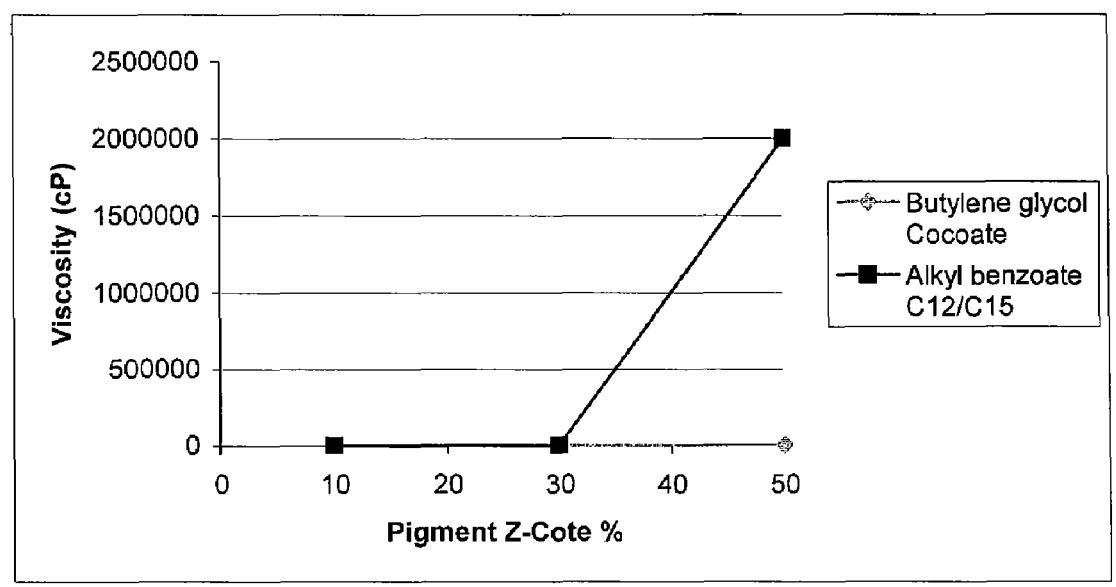
Figure 1C:
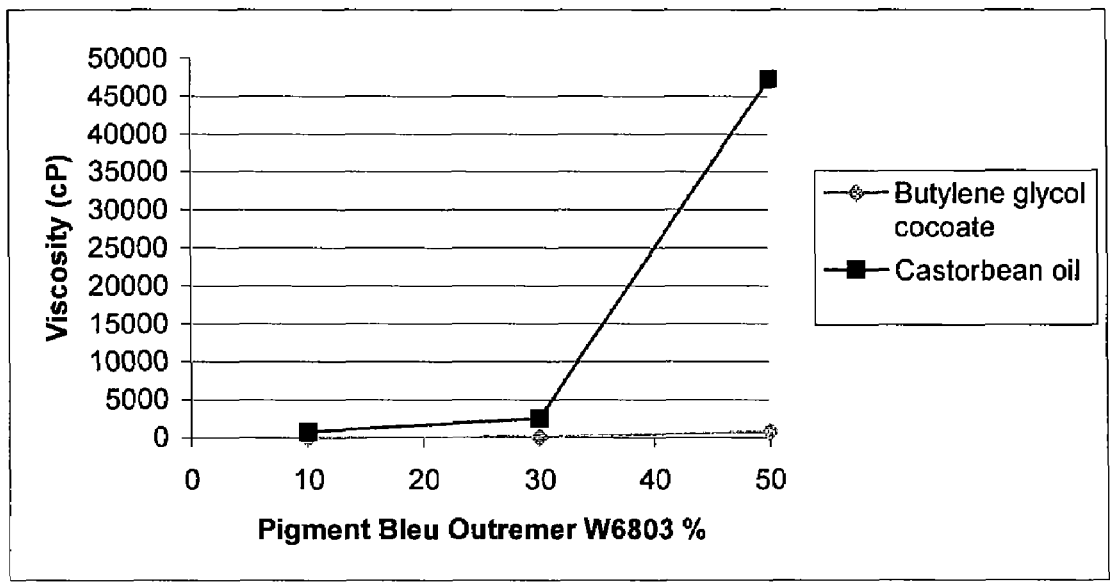
Figure 1D:
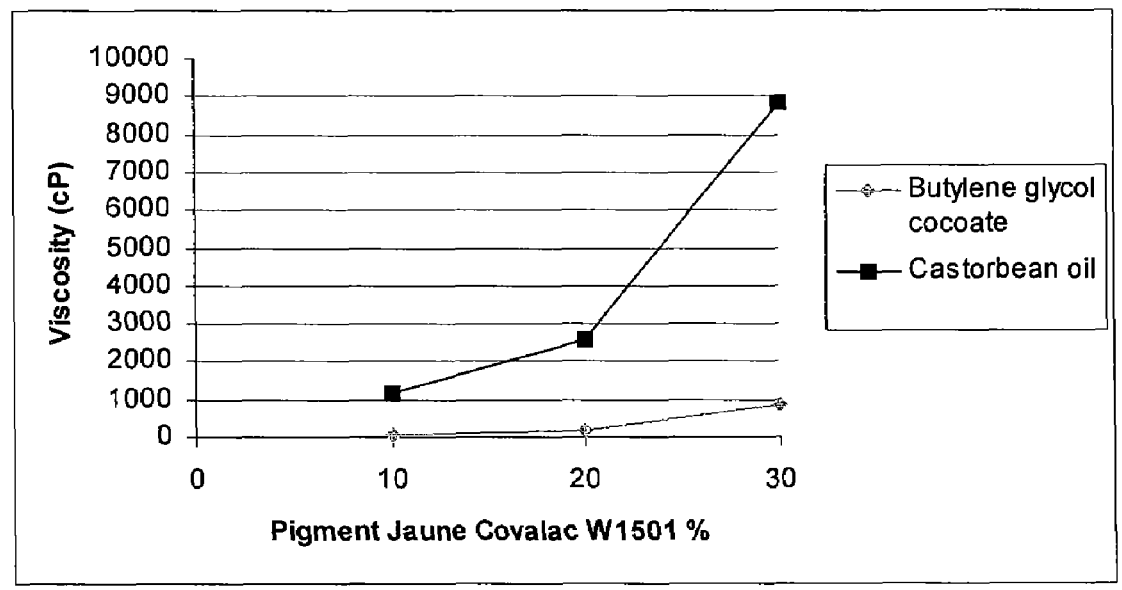

Accordingly, the invention relates to the use of a mixture of monoesters and diesters of butylene glycol and fatty acids as a wetting agent.

According to a first feature, the fatty acids are selected from the group comprising $C_6$ to $C_{22}$ fatty acids. Obviously, the monoesters and diesters may be obtained from different and/or identical fatty acids, saturated and/or unsaturated.

In one particular embodiment, the wetting agent of the invention is obtained by esterification of butylene glycol with all or part of fatty acids of natural origin, particularly issuing from vegetable oil.

The Applicant has found that good results were obtained when lauric acid accounted for at least 40%, advantageously between 50 and 60% by weight of the fatty acids. Such a distribution is found in coconut or palm oil.

Therefore and according to a preferred embodiment, the wetting agent is obtained by esterification of butylene glycol and of a fraction of $C_{12}$ to $C_{18}$ fatty acids issuing from coconut oil.

According to another feature, the monoesters account for between 10 and 90%, advantageously between 40 and 60% by weight of the monoester/diester mixture.

The wetting agent described has technological importance because it facilitates the formulation method. In fact, it is used in a lower proportion for a given quantity of pigments in comparison with conventional wetting agents. It procures a lower viscosity of the dispersions. They are therefore easier to use than those obtained with conventional wetting agents. Finally, the smaller quantity of wetting agent of the invention to be used serves to allow for texture or touch agents which can be incorporated in the formula. Moreover, this wetting agent procures a dry, non-greasy touch.

As already stated, this product can be used in all cosmetic or dermatological compositions comprising pigments useful, due to its wetting properties, for improving the dispersion in the oily phase, and for optimizing the spreading of the composition on the skin. Obviously, the proportion of wetting agent in the composition depends on the type and quantity of the pigments used.

In particular, the use of the agent of the invention is particularly advantageous in products containing pigments such as solar products, make-up products (foundation creams, mascara, lipstick, etc.), baby creams incorporating pigments or products for removing the pigments such as make-up cleansing products.

The compositions into which the wetting agent of the invention can be introduced may be in the form of a water-in-oil, oil-in-water, multiple emulsion, or in anhydrous form.

They may also contain the usual additives in the cosmetic and dermatological fields, such as fatty materials, emulsifiers and co-emulsifiers, hydrophilic or lipophilic gelling agents, hydrophilic or lipophilic agents, preservatives, antioxidants, solvents, perfumes, fillers, hydrophilic and lipophilic filters, colorants, neutralizers, pro-penetrants, and polymers. The quantities of these various additives are those conventionally used in the areas considered, and for example 0.01 to 30% of the total weight of the composition. These additives, depending on their type, may be introduced into the fatty phase or into the aqueous phase.

As fatty materials, use can be made of mineral oils, of animal origin (lanolin), synthetic oils (isopropyl myristate, octyldodecyl, isostearyl isostearate, decyl oleate, isopropyl palmitate), silicone oils (cyclomethicone, dimethicone) and fluorinated oils. As fatty materials, use can be made of fatty alcohols, fatty acids, waxes and gums, and particularly silicone gums.

As examples of usable emulsifiers and co-emulsifiers, mention can be made of esters of polyglycerols and fatty acids, esters of sucrose and fatty acids, esters of sorbitane and fatty acids, esters of fatty acids and oxyethelene sorbitane, ethers of fatty alcohols and PEG, esters of glycerol and fatty acids, alkyl sulphates, alkyl ether sulphates, alkyl phosphates, alkyl polyglucosides, and dimethicone copolyols.

As hydrophilic gelling agents, mention can be made particularly of carboxyvinyl polymers (carbomer), acrylic copolymers such as copolymers of acrylates/alkylacrylates, polyacrylamides polysaccharides such as gum xanthan, gum guar, natural gums such as cellulose gum and derivatives, and clays.

As lipophilic gelling agents, mention can be made of modified clays such as bentones, metal source of fatty acids, hydrophobic silica and ethylcellulose.

As active agents, use can be made particularly of pigment removers, emollients, moisturizers, anti-seborrhoeics, anti-acne agents, keratolytic and/or peeling agents, anti-wrinkle agents and tensors, draining agents, anti-irritants, soothing agents, thinning agents such as xanthic bases (caffeine), vitamins and mixtures thereof.

As usable preservatives, mention can be made of benzoic acid, its salts and esters; sorbic acid and salts thereof; parabens, salts and esters thereof; triclosan; imidazolidinyl urea; phenoxyethanol; hydantoin DMDM; diazolidinyl urea; chlorphenesin.

As usable antioxidants, mention can be made of cheletants such as EDTA and salts thereof.

As usable solvents, mention can be made of water, ethanol, glycerine, propylene glycol, butylene glycol, and sorbitol.

As usable fillers, mention can be made of talc, kaolin, mica, serecite, magnesium carbonate, aluminium silicate, magnesium silicate, and organic powders such as nylon.

As usable filters, mention can be made of UVA and UVB filters conventionally used such as benzophenone-3, butyl methoxydibenzoyl methane, octocrylene, octyl methoxycinnamate, 4-methylbenzylidene camphor, octyl salicylate.

As usable dyes, mention can be made of lipophilic dyes, hydrophilic dyes, and mother of pearl commonly used in cosmetic or dermatological compositions, and mixtures thereof.

As usable neutralizers, mention can be made of caustic soda, triethanolamine, aminomethyl propanol, and potassium hydroxide.

It is also possible to propose formulations corresponding to dispersions based exclusively on pigments and of the wetting agent of the invention. A stabilizer of the polymer type can be incorporated, to prevent the pigments from settling. The dispersion then remains smooth and uniform. This dispersion may also contain lipophilic phases of the oil or ester type. This dispersion can then be incorporated as such into the more complex cosmetic composition.

BRIEF SUMMARY OF THE DRAWING FIGURES

The invention and its advantages will appear clearly from the following exemplary embodiments, in conjunction with the figures appended hereto.

FIGS. 1a, b, c and d are curves showing the viscosity of a dispersion formulated with the wetting agent of the invention or an agent of the prior art ($C_{12}$ to $C_{15}$ alkyl benzoate or castor oil) as a function of an increasing quantity of pigments.

Figure 2A:
FIG. 2a is a photograph taken with the optical microscope (magnification ×400) of a pigmented emulsion formulated with BGC.
Figure 2B:
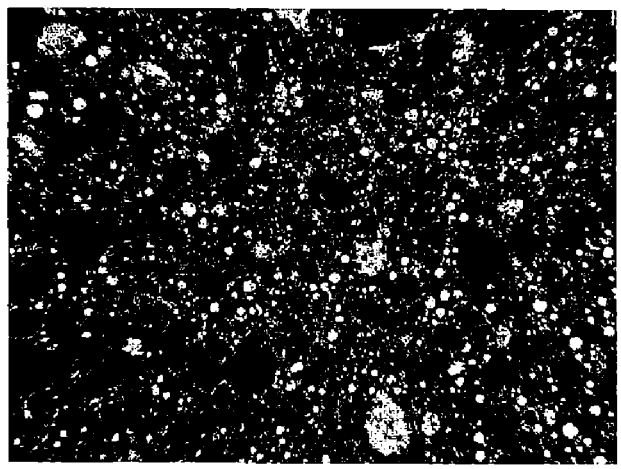
FIG. 2b is a photograph taken with the optical microscope (magnification ×400) of a pigmented emulsion formulated with $C_{12}$ to $C_{15}$ alkyl benzoate.

FIG. 2 are photographs taken with the optical microscope (magnification ×400) of a pigmented emulsion formulated with BGC (FIG. 2A) or with $C_{12}$ to $C_{15}$ alkyl benzoate (FIG. 2B).

DETAILED DESCRIPTION

Example 1

Wetting Power and Viscosity Compared with Various Wetting Agents

1. Evaluation of Wetting Power

The wetting power of an oil or a solvent is the minimum quantity of oil or solvent necessary to form a smooth paste with a powder, without cracking during its spreading.

It is expressed as grams of oil necessary to wet 100 g of pigment. The smaller the quantity of oil required, the higher the wetting power.

2. Results of Wetting Power Compared with Conventional Wetting Agents
   2.a. Wetting Power

TABLE 1

Quantity of wetting agent, in g, necessary to disperse 100 g of pigment

| Wetting Agent | Pigments | | | | | | | |
|---|---|---|---|---|---|---|---|---|
| | TiO2 PW* | TiO2 W 877* | ZnO Z Cote** | Ultramarine Blue W 6803* | Brown W8802* | Black W9814* | Red W3801* | Yellow covalac W 1501* |
| Butylene Glycol Cocoate | 114 | 21 | 60 | 62 | 25 | 37 | 27 | 110 |
| C12/C15 Alkyl Benzoate | 174 | 32 | 99 | 79 | 47 | 63 | 59 | 162 |
| Castor Oil | | 27 | | 88 | 31 | 46 | 39 | 97 |
| Isopropyl Palmitate | | 26 | | 70 | 42 | 56 | 49 | 132 |
| Caprylic/Capric Triglycerides | | 29 | | 80 | 44 | 57 | 54 | 147 |

*Sold by LCW
**Sold by BASF

As shown by the table, butylene glycol cocoate yields better results. Moreover, even if the castor oil gives a result that may appear satisfactory, in certain cases, its high viscosity makes the product difficult to use.

2.b. Viscosity of Dispersions

FIGS. 1*a, b, c* and *d* are curves showing the viscosity of a dispersion formulated with the wetting agent of the invention or an agent of the prior art (C12 to C15 alkyl benzoate or castor oil) as a function of an increasing quantity of pigments.

The dispersions obtained with BGC are more fluid than with $C_{12}$ to $C_{15}$ alkyl benzoate or castor oil. Thus for the same composition, a dispersion in BGC is easier to use.

3. Results of Wetting Power Compared with a Butylene Glycol Diester

TABLE 2

Quantity of wetting agent, in g, necessary to disperse 100 g of pigment

| Wetting agents | Pigments | | | | | | |
|---|---|---|---|---|---|---|---|
| | TiO2 W 877 | ZnO Z Cote | Ultramarine Blue W 6803 | Yellow covalac W 1501 | Brown W8802 | Black W9814 | Red W3801 |
| Butylene Glycol Cocoate | 21 | 60 | 62 | 110 | 25 | 37 | 27 |
| Butylene Glycol Dicaprylate/Dicaprate | 30 | 92 | 71 | 140 | 51 | 62 | 56 |
| Butylene Glycol Dicocoate | 25 | 66 | 67 | 130 | | | |

As shown by the table, the wetting agent of the invention is more effective than the product described in the prior art (EP-A-1 230 910), used as a filter solubilizing agent.

Conclusion: The inventive product, a mixture of monoester and diester, is more effective than a diester.

4. Result of Wetting Power Compared with Glycol Esters (Monoesters and Diesters)

| Wetting agents | Pigments | |
|---|---|---|
| | TiO2 W 877 | Ultramarine Blue W 6803 |
| Butylene Glycol Cocoate | 21 | 62 |
| Propylene Glycol Caprylate | 26 | 72 |
| Propylene Glycol Laurate | 23 | 70 |
| Propylene Glycol Dicaprylate/Dicaprate | 28 | 76 |
| Propylene Glycol Isostearate | 23 | 73 |

Conclusion: Regardless of the type or length of the fatty chain (giving a liquid product), BGC yields a better result than the propylene glycol esters (diesters or mixture of mono/diesters) or the butylene glycol diesters.

Example 2

Evaluation in Formulation

Measurement of Solar Protection Factor (SPF)

The excellent wetting power demonstrated for BCG finds an interesting application in solar products containing mineral filters such as titanium dioxide and zinc oxide. In fact, a better wetting of these pigments in a formulation allows a better dispersion and better spreading thereof on the skin, hence better solar protection.

Two oil-in-water emulsions were formulated respectively with BGC (A) and $C_{12}$-$C_{15}$ alkyl benzoate (B).

|  |  | A | B |
|---|---|---|---|
| Phase I | Emulium ® 22 | 4 | 4 |
|  | Mineral oil | 2 | 2 |
|  | Dimethicone | 2 | 2 |
|  | Butylene Glycol Cocoate | 23 | — |
|  | C12-C15 alkyl benzoate | — | 23 |
|  | Titanium Dioxide | 10 | 10 |
|  | Zinc Oxide | 5 | 5 |
|  | Preservative | qs | qs |
| Phase II | Deionized water | Qsp 100 | Qsp 100 |
|  | Gum xanthan | 0.4 | 0.4 |
|  | Microcrystalline cellulose and cellulose gum | 1 | 1 |
|  | Glycerine | 3 | 3 |

FIG. 2 are photographs taken with the optical microscope (magnification ×400) of a pigmented emulsion formulated with BGC (FIG. 2A) or with a $C_{12}$-$C_{15}$ alkyl benzoate (FIG. 2B).

A wide difference can be found in the dispersion of the pigments. In fact, in formula A containing BGC (FIG. 2A), the pigments are well dispersed, whereas in formula B containing $C_{12}$-$C_{15}$ alkyl benzoate (FIG. 2B), the pigments appear in the form of aggregates.

The solar protection factors were measured in vivo according to the recommendations of COLIPA on 5 volunteers:

| Formula A | Formula B |
|---|---|
| 11.5 +/− 2.9 | 8.7 +/− 2.8 |

These results show significantly ($p<0.05$) that the use of BGC instead of $C_{12}$-$C_{15}$ alkyl benzoate serves to obtain a higher solar protection factor (SPF).

Furthermore, at the sensory level, formula A is significantly easier to spread on the skin than formula B.

Example 3

Formulas

A few examples of formulas are given below, preparable with the dispersions of pigments containing BGC in several applications.

1. Solar

Water-in-Oil Solar Cream:

|  | Ingredients | % m/m |
|---|---|---|
| Phase I | Diisostearic Plurol ® | 5 |
|  | Butylene Glycol Cocoate | 10 |
|  | Isohexadecane | 10 |
|  | Dimethicone and dimethiconol | 2 |
|  | Titanium dioxide | 10 |
|  | Preservative | qs |
| Phase II | Deionized water | Qsp 100 |
|  | MgSO4•7H2O | 0.5 |
|  | NaCl | 0.5 |
|  | Glycerine | 3 |

The SPF of the formula was measured at 21 in vivo.

|  | Ingredients | % m/m |
|---|---|---|
| Phase I | Cetyl Dimethicone Copolyol | 3.50 |
|  | Diisostearyl Polyglyceryl-3 Dimer Dilinoleate | 1.50 |
|  | Octyl Methoxycinnamate | 7.50 |
|  | Octocrylene | 2.00 |
|  | Cyclomethicone | 8.00 |
|  | Tocopherol Acetate | 0.50 |
|  | Preservative | Qs |
| Phase II | Butylene Glycol Cocoate | 10.00 |
|  | Titanium dioxide & Trimethoxycaprylylsilane | 10.00 |
| Phase III | Deionized water | Qsp 100 |
|  | NaCl | 0.50 |
|  | Glycerine | 3.00 |

The Solar Protection Factor (SPF) of the formula was measured at 43.6 in vivo.

2. Make-Up

Foundation Cream

|  | Ingredients | % m/m |
|---|---|---|
| Phase I | Hydrolactol ® 70 | 5 |
|  | Cetostearyl alcohol | 2 |
|  | Cetyl alcohol | 1 |
|  | Dimethicone | 4 |
|  | Cyclomethicone | 2 |
|  | Isostearyl isostearate | 5 |
|  | Preservative | qs |
| Phase II | Deionized water | Qsp 100 |
|  | Microcrystalline cellulose and cellulose gum | 1.5 |
|  | Gum xanthan | 0.4 |
|  | EDTA, Na2 | 0.1 |
| Phase III | Butylene Glycol Cocoate | 3 |
|  | Titanium Dioxide | 6.6 |
|  | Yellow iron oxide | 1.2 |
|  | Brown pigment | 0.25 |
|  | Red iron oxide | 0.53 |
|  | Black iron oxide | 0.11 |

Mascara

|  | Ingredients | % m/m |
|---|---|---|
| Phase I | Apifil ® | 8 |
|  | Compritol ® 888 | 2 |
|  | Dimethicone | 2 |
| Phase II | Deionized water | Qsp 100 |
|  | Carbomer | 0.2 |
| Phase III | 10% caustic soda | 0.4 |
| Phase IV | Butylene Glycol Cocoate | 8 |
|  | Black iron oxide | 12 |
|  | Talc | 4 |
| Phase V | PVP/Dimethylaminoethyl methacrylate copolymer | 10 |
|  | Preservative | Qs |

3. Lipstick

| Ingredients | % m/m |
|---|---|
| Lipstick base CB8047 (Gattefossé) | 73.35 |
| Candelilla wax | 4 |
| Ozokerite | 2 |

-continued

| | Ingredients | % m/m |
|---|---|---|
| | Ethoxydiglycol Behenate | 8 |
| | Butylene Glycol Cocoate | 8 |
| | Covalac Yellow W1501 | 2 |
| | Covanor Ruby W4605 | 1 |
| | Titanium dioxide W877 | 1.65 |

4. Cleansing Agent

Cleansing Milk

| | Ingredients | % m/m |
|---|---|---|
| Phase I | Deionized water | Qsp 100 |
| | Acrylic polymer | 0.3 |
| | Gum xanthan | 0.2 |
| | Preservative | qs |
| Phase II | Butylene Glycol Cocoate | 10 |
| | Cyclomethicone | 2 |
| Phase III | 10% Caustic soda | 0.6 |

5. Baby Products

Baby Cream with Zinc Oxide

| | Ingredients | % m/m |
|---|---|---|
| Phase I | Diisostearic Plurol ® | 5 |
| | Mineral oil | 15 |
| | Butylene Glycol Cocoate | 7 |
| | Zinc oxide | 15 |
| | Compritol ® 888 | 5 |
| | Preservative | Qs |
| Phase II | Deionized water | Qsp 100 |
| | NaCl | 0.5 |
| | MgSO4•7H2O | 0.5 |
| Phase III | Extract of *Calendula officinalis* | 2 |
| | Perfume | qs |

The invention claimed is:

1. A method of wetting a pigment comprising mixing said pigment with a mixture comprising:
   a) at least one monoester of butylene glycol; and
   b) at least one diester of butylene glycol,
wherein said monoester and diester of butylene glycol are esters of fatty acids.

2. A method according to claim 1, wherein the fatty acids are selected from the group consisting of $C_6$-$C_{22}$ fatty acids.

3. A method according to claim 1, wherein the monoester and diester are a monoester and diester of one or more saturated fatty acids, one or more unsaturated fatty acids, or combinations thereof.

4. A method according to claim 1, wherein the acyl portion of said ester is the acyl residue of a fatty acid of natural origin.

5. A method according to claim 1, wherein lauric acid represents at least 40% by weight of the fatty acids.

6. A method according to claim 1, wherein the acyl portion of said ester is the acyl residue of a $C_{12}$ to $C_{18}$ fatty acid found in coconut oil.

7. A method according to claim 1, wherein the monoesters represent between 10 and 90% by weight of the mixture.

8. A method according to claim 4, wherein the fatty acids of natural origin comprise fatty acids found in vegetable oil.

9. A method according to claim 5, wherein lauric acid represents between 50% and 60% by weight of the fatty acids.

10. A method according to claim 7, wherein the monoesters represent between 40% and 60% by weight of the mixture.

11. A dispersion comprising:
   a) a pigment; and
   b) a mixture of at least one monoester and at least one diester of butylene glycol, said esters being esters of fatty acids.

12. A dispersion according to claim 11, further comprising a stabilizer.

13. A dispersion according to claim 11, further comprising at least one lipophilic phase.

14. A dispersion according to claim 13, further comprising a stabilizer.

* * * * *